(12) United States Patent
Todd et al.

(10) Patent No.: US 8,436,727 B2
(45) Date of Patent: May 7, 2013

(54) METHODS AND SYSTEMS FOR DOOR ACCESS AND PATIENT MONITORING

(76) Inventors: James D. Todd, Garnett, KS (US);
Thomas Hollinger, Overland Park, KS (US); Christopher F. Fangrow, Harrisonville, MO (US)

(*) Notice: Subject to any disclaimer, the term of this patent is extended or adjusted under 35 U.S.C. 154(b) by 378 days.

(21) Appl. No.: 12/895,534

(22) Filed: Sep. 30, 2010

(65) Prior Publication Data
US 2011/0128145 A1    Jun. 2, 2011

Related U.S. Application Data

(60) Provisional application No. 61/247,327, filed on Sep. 30, 2009.

(51) Int. Cl.
| | |
|---|---|
| *G08B 1/08* | (2006.01) |
| *B60R 25/00* | (2006.01) |
| *E05B 53/00* | (2006.01) |
| *A61B 5/00* | (2006.01) |
| *G05B 19/00* | (2006.01) |

(52) U.S. Cl.
USPC .............. 340/539.11; 340/539.12; 340/573.1; 340/539.23; 340/542; 340/5.2; 340/286.07; 340/5.7; 70/263

(58) Field of Classification Search ............. 340/539.11, 340/539.12, 539.23, 542, 5.2, 286.07; 70/263
See application file for complete search history.

(56) References Cited

U.S. PATENT DOCUMENTS

| | | | |
|---|---|---|---|
| 5,878,450 A | 3/1999 | Bouhuijs | |
| 6,084,513 A | 7/2000 | Stoffer | |
| 6,134,725 A | 10/2000 | Bouhuijs | |
| 6,396,413 B2 * | 5/2002 | Hines et al. | 340/8.1 |

(Continued)

FOREIGN PATENT DOCUMENTS

WO    WO2010031694 A1    3/2010

OTHER PUBLICATIONS

TeleAlarm, NurseCall Main Unit, User Manual, 953.92, v1.0, dated Aug. 2007 (92 pages).

(Continued)

*Primary Examiner* — Donnie Crosland
(74) *Attorney, Agent, or Firm* — Polsinelli Shughart PC

(57) ABSTRACT

Methods and systems for door access and patient monitoring are described. The patient monitoring system includes a door access control system coupled to one or more doors of a facility for monitoring and controlling the access of patients coupled to a patient monitoring device. Whenever a patient coupled to a patient monitoring device comes within a predetermined distance of a particular door the door access control system transmits a first signal encoded with the door location data to the patient monitoring device. The patient monitoring device then transmits a second signal encoded with the door location data and patient identification data of the patient coupled to the monitoring device to the door access control system and a monitoring system that controls the door access and monitoring of patient within the facility. If the door coupled to the door access control system is in the open position when the patient is detected, the door access control system transmits a third signal encoded with the door location data to the monitoring system. The monitoring system then compares the door location data encoded in the second signal with the door location data encoded in the third signal before displaying that data at a master station for alerting facility staff.

29 Claims, 11 Drawing Sheets

U.S. PATENT DOCUMENTS

| | | | |
|---|---|---|---|
| 6,972,660 B1 * | 12/2005 | Montgomery et al. | 340/5.52 |
| 6,972,677 B2 | 12/2005 | Coulthard | |
| 7,554,446 B2 * | 6/2009 | Ciarcia et al. | 340/568.1 |
| 2004/0189471 A1 * | 9/2004 | Ciarcia et al. | 340/572.1 |
| 2005/0052275 A1 | 3/2005 | Houle | |
| 2006/0235283 A1 | 10/2006 | Vinarov et al. | |
| 2007/0163045 A1 | 7/2007 | Becker et al. | |

OTHER PUBLICATIONS

2000 Series e/eM Style Keypad Installation and Programming Manual, Document No. 6054022, Revision: 1.0, dated Dec. 21, 2006 (60 pages).

TeleAlarm, LLC, LE9 Road (Resident Out-of-Bed Activity Module) Specification Sheet, date unknown (2 pages).

D. Schwendener, TeleAlarm, Wireless Contact RAC (434)—Set-up Information, Janvier 2006 Document No. 953-36 (4 pages).

TeleAlarm, NurseCall Relay Unit, Data Sheet, Reference Nos. NC.021.FI, XX, dated Jun. 3, 2006 (2 pages).

TeleAlarm, IS 76 Beacon with Ferrite Antenna, Installation Manual, Document 953.26 (11 pages).

Senior Technologies, WanderGuard Delayed Egress Magnetic Locks—17000 Series (2 pages).

Senior Technolgoies, Arial Options, Wireless Communication Systems, date unknown (1 page).

Senior Technologies, WanderGuard, Departure Alert System, WanderGuard ID Departure Alert System, Model 16921, undated (2 pages).

Senior Technologies, WanderGuard System Hospital, Product Information, undated (1 page).

Senior Technologies, Products and Services, undated (1 page).

Senior Technologies, WanderGuard System Long-Term Care, Product Information, undated (1 page).

Senior Technologies, WanderGuard System Residential Community, Product Information, undated (1 page).

* cited by examiner

METHODS AND SYSTEMS FOR DOOR ACCESS AND PATIENT MONITORING

RELATED APPLICATIONS

This application takes priority to U.S. Patent Application No. 61/247,327, filed Sep. 30, 2009 and entitled Methods and Systems for Door Access and Patient Monitoring, the entire contents of which are incorporated herein by reference.

FIELD

This application relates to methods and systems for door access and patient monitoring, and more specifically to methods and systems for door access and monitoring of patients in a controlled access environment.

BACKGROUND

Healthcare facilities including hospitals, nursing homes and assisted living residences have often encountered problems with patients/residents (either intentionally or inadvertently) leaving designated areas or facility grounds. Concerns with wandering patients are particularly prevalent when those patients have Alzheimer's disease, as the disease is one of the most common forms of dementia causing both memory loss and general confusion.

Many healthcare facilities today have door access and monitoring systems to alleviate the problems with wandering patients, but those systems are often simplistic and not multifaceted. Some healthcare facilities have special access facilities requiring an entry code or programmed badge to open doors; however, Alzheimer's patients often "tailgate" behind authorized personnel through before the door closes and locks, unbeknownst to staff.

Traditional door access and monitoring systems are also employed at healthcare facilities, but these systems are at times not 100% reliable. Many times these systems also run the risk of false alarms burdening staff, patients, and visitors. This can occur, for example, when patients in non-designated areas but are accompanied/escorted by staff pass through secured doors, thus setting off an alarm. Thus, healthcare facilities today still deal with both glitches and annoyances in door access and monitoring systems for Alzheimer's patients as well as errors in the systems leading to liability. Patient door access and monitoring systems can also be utilized for other healthcare facility concerns, besides Alzheimer's, such as monitoring newborn babies, brain injury patients and other types of patients that require constant monitoring within a healthcare facility.

DETAILED DESCRIPTION

Example methods and systems for door access and patient monitoring are described. In the following description, for purposes of explanation, numerous specific details are set forth in order to provide a thorough understanding of example embodiments. It will be evident, however, to one of ordinary skill in the art that embodiments of the invention may be practiced without these specific details.

Figure 1:
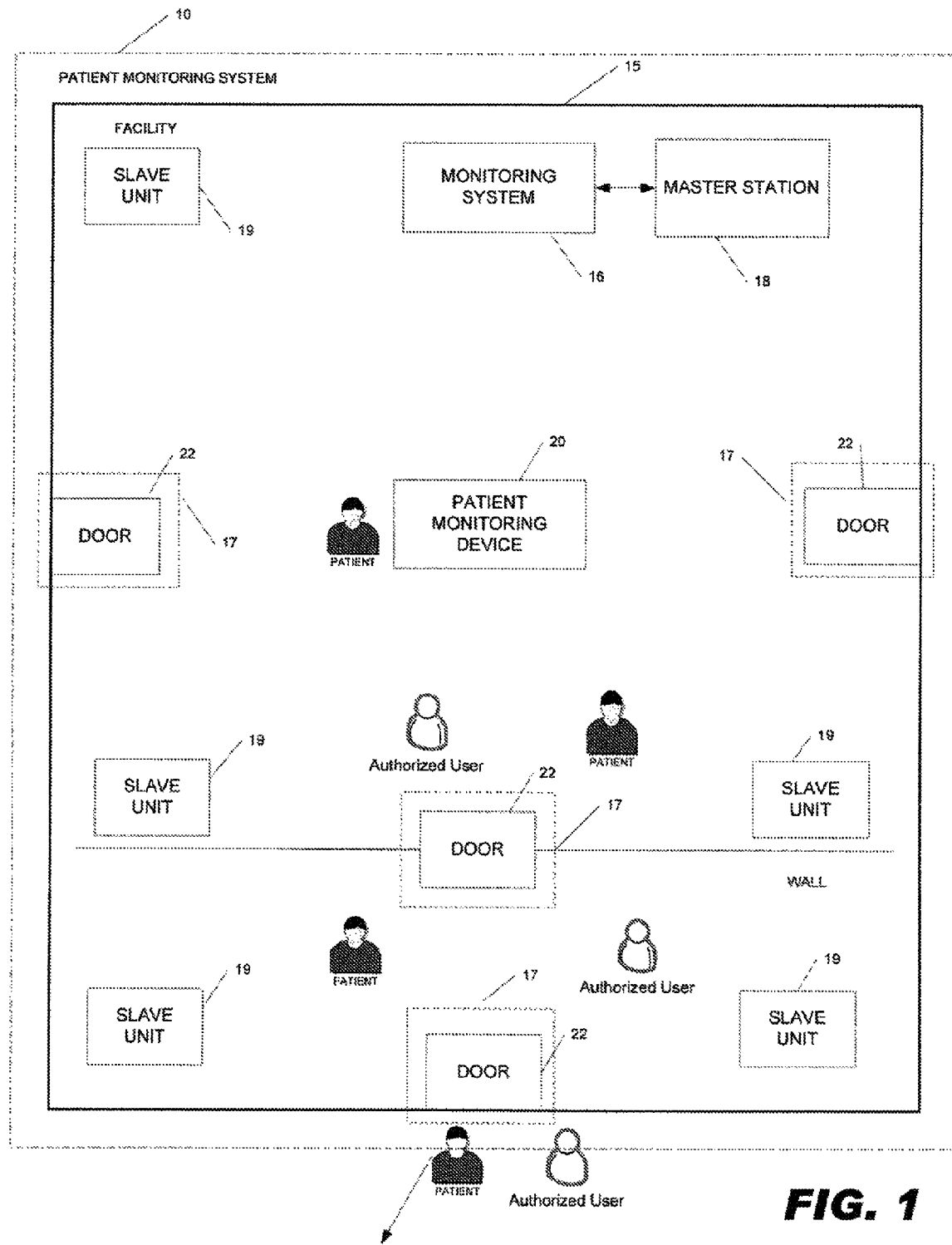
FIG. 1 is a simplified block diagram of the patient monitoring system within a facility.

Referring to the drawings, an embodiment of the patient monitoring system is illustrated and generally indicated as 10 in FIG. 1. In an example embodiment of the patient monitoring system 10, one or more patients or other persons to be monitored within a facility 15 may have a patient monitoring device 20 coupled to his or her wrist or ankle in a secure manner that prevents the patient from removing the patient monitoring device 20. When a patient monitoring device 20 is coupled to each patient within the facility 15 the patient monitoring system 10 has the capability of detecting, securing and monitoring any patient coupled to a patient monitoring device 20 who comes within close proximity or a predetermined distance to any door 22 of the facility 15. In addition, the patient monitoring system 10 includes a plurality of door access control systems 17 that are each coupled and operatively associated with a respective door 22. The door access control system 17 has the capability to detect the presence of any person in close proximity to the door 22, and in particular to detect and identify the presence of a patient by virtue of the patient being coupled to the patient monitoring device 20. In one embodiment, the door access control system 17 may lock down the door 22 when the presence of the patient coupled to a patient monitoring device 20 is detected. As used herein, the term "lock down" refers to the capability of the door access control system 17 to prevent the door 22 from being opened once the door 22 is closed. In other embodiments the door 22 may be locked down at all times unless an access code is entered into the door access control system 17. As also used herein, the term "door" may refer to any swinging or sliding barrier by which an entry is closed and opened, or hallway leading to a non designated area.

Referring to FIGS. 1, 2, 3 and 4, each patient monitoring device 20 includes a receiver 68 for receiving a first signal 96 transmitted by the door access control system 17 whenever any person coupled to a patient monitoring device 20 comes within close proximity of a door 22 having a door access control system 17. Moreover, the patient monitoring device 20 has a memory 64 including patient identification data 72 for identifying the patient wearing or otherwise coupled to a particular patient monitoring device 20. The patient monitoring device 20 further includes a transmitter 66 that transmits the second signal 97 encoded with patient identification data 72 stored in memory 64 as well as the door location data 70 that was originally encoded in the first signal 96 transmitted by the door access control system 17 to the patient monitoring device 20. The second signal 97 is transmitted directly to the door access control system 17 as well as being transmitted to a monitoring system 16 through a wireless network 13 in response to receiving the first signal 96 transmitted by the door access control system 17 as shall be discussed in greater detail below.

The wireless network 13 includes a master station 18 that is in communication with a plurality of slave units 19 arranged within the facility 15 to provide optimum coverage around the facility 15 for receiving wireless signals being transmitted by the patient monitoring device 20. The communication may be made in a serial or parallel manner. The master station 18 communicates with the monitoring system 16 to control the operation of the patient monitoring system 10. In one embodiment, the monitoring system 16 includes a database 39 containing door location data 70 that identifies the location of each door 22 in the facility 15 by using a unique identification code. In addition, the database 39 includes patient identification data 72 that identifies each patient coupled to a particular patient monitoring device 20. In one embodiment, the patient monitoring device 20 may be an SL37L426 Wristband Transmitter with Locating Function manufactured by BOSCH, while the master station 18 may be a NurseCall Main Unit and each of the plurality of slave units 19 may be a NurseCall Relay Unit which are both manufactured by BOSCH.

Figure 2:
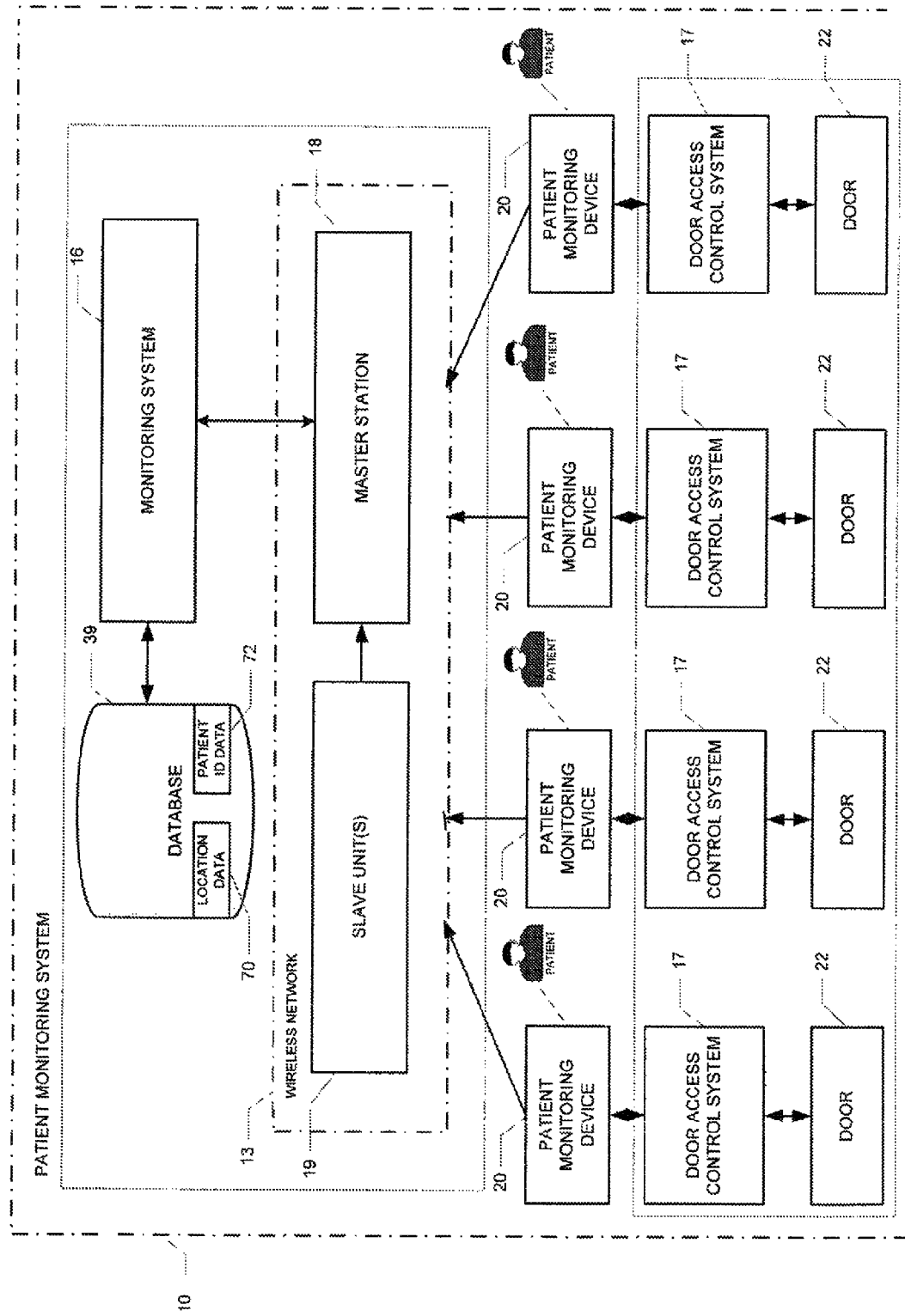
FIG. 2 is a simplified block diagram of the patient monitoring system.

As shown in FIGS. 1 and 2, the patient monitoring system 10 may be configured such that each respective door access control system 17 controls the monitoring and access for one particular door 22 in the facility 15. As shown, one or more doors 22 may control access to facility 15, while other doors 22 may control access to areas within the facility 15. In one embodiment, the door access control system 17 may be directly hardwired to the monitoring system 16, although wireless communication with the monitoring system 16 is also contemplated. In this arrangement, the patient monitoring system 10 may monitor and control access to a plurality of doors 22 within the facility 15 through either the monitoring system 16, or in the alternative, through a fail-safe operation system 30 that becomes operational whenever the monitoring system 16 becomes disabled and non-operational as shall be discussed in greater detail below.

Figure 3:
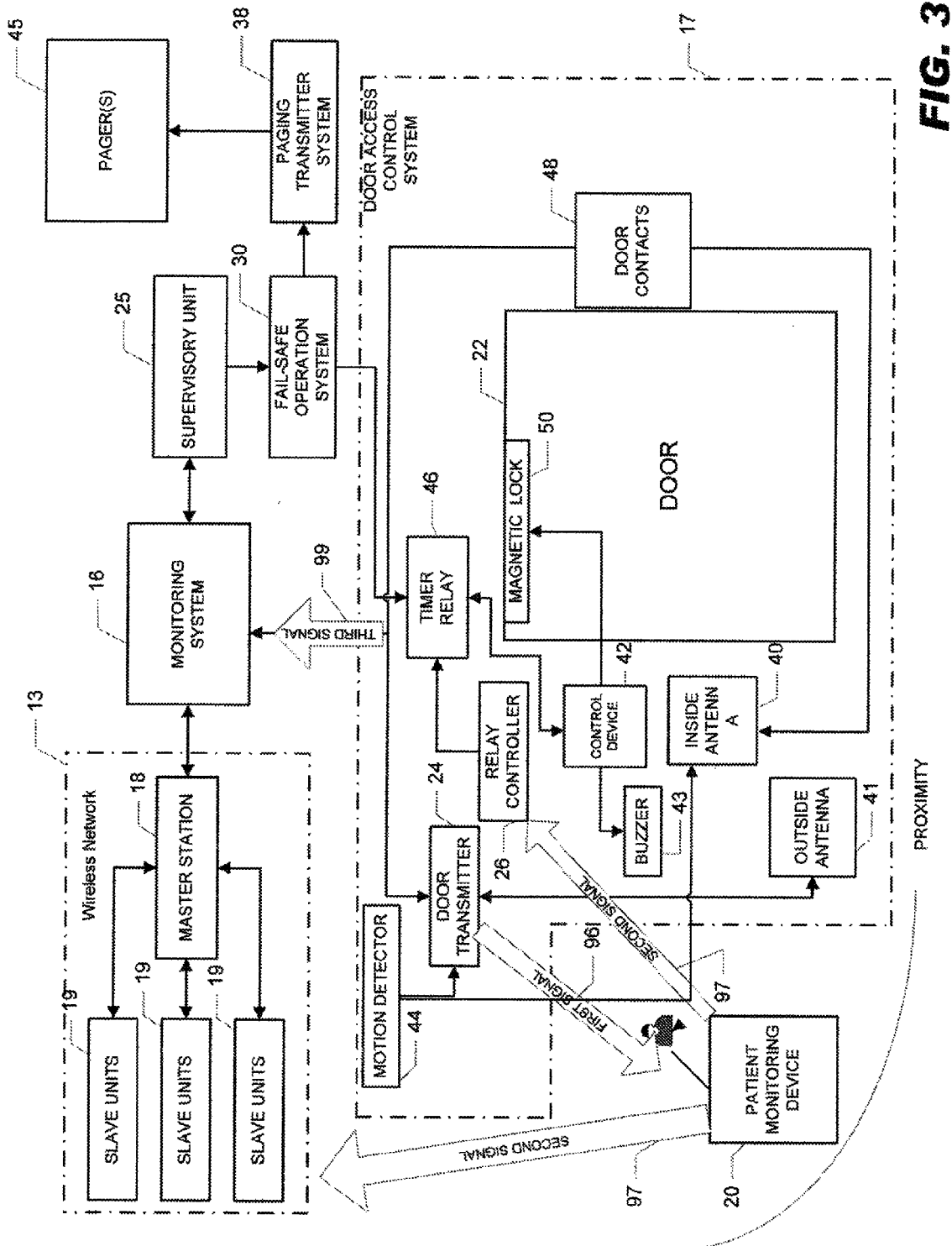
FIG. 3 is a simplified block diagram of a door access control system and wireless network of the patient monitoring system.
Figure 4:
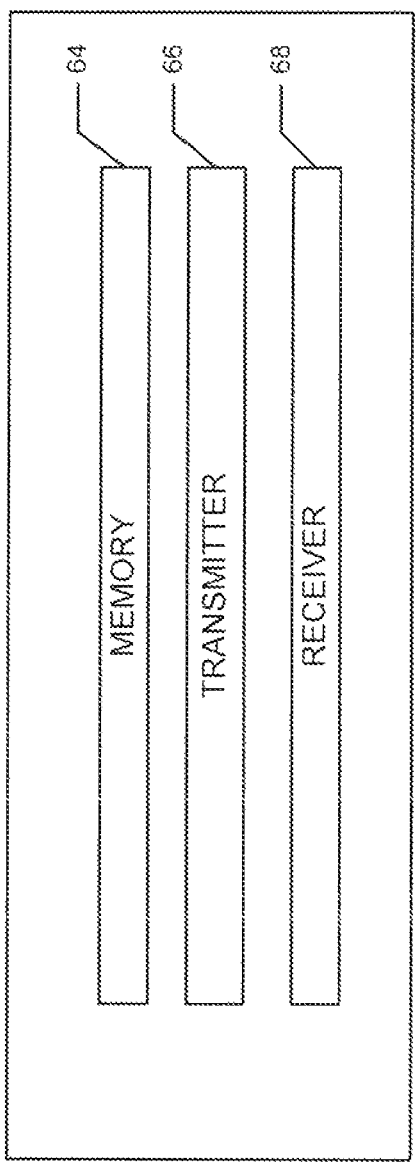
FIG. 4 is a simplified block diagram of a patient monitoring device for the patient monitoring system.

Referring to FIG. 3, the door access control system 17 includes a motion detector 44 that actuates a door transmitter 24 through an inside antenna 40 for transmitting the first signal 96 whenever a person comes within a predetermined distance or proximity of the motion detector 44. In one embodiment, the door transmitter 24 for transmitting the first signal 96 may be an I76 Beacon with Ferrite Antenna manufactured by BOSCH. The actuation of the door transmitter 24 by the motion detector 44 when triggered by a person that comes within proximity of the motion detector 44 actuates the inside antenna 40 and causes the door transmitter 24 to transmit through the inside antenna 40 the first signal 96. The first signal 96 is encoded with door location data 70 that identifies the particular door 22 of the facility 15.

If the person who triggered the motion detector 44 is coupled to a patient monitoring device 20, the receiver 68 of the patient monitoring device 20 will receive the first signal 96 transmitted by the door transmitter 24. The patient monitoring device 20, in response, then transmits through transmitter 66 the second signal 97 encoded with the door location data 70 derived from the received first signal 96 as well as patient identification data 72 stored in memory 64 of the patient monitoring device 20. The transmission of the second signal 97 by the patient monitoring device 20 is received by both the door access control system 17 through the inside antenna 40 as well as by one or more of the plurality of slave units 19 and/or the master station 18 arranged within the facility 15 which is then communicated directly to the monitoring system 16 by the master station 18.

The door transmitter 24 may be hardwired to a plurality of door contacts 48 that detect the open or close positions of the door 22. One or more of the plurality of door contacts 48 may also be hardwired to the inside antenna 40 which is actuated when either the door 22 is opened, or the motion detector 44 detects the presence of the person in proximity to the door 22 for transmitting the first signal 96 to any patient monitoring device 20 in close proximity to door 22. In one embodiment, the door transmitter 24 may also be hardwired to an outside antenna 41 that is always operational and permits transmission of the first signal 96 by the door transmitter 24 outside of the facility 15, or receive the second signal 97 transmitted by the patient monitoring device 20 in response to the first signal 96.

The door access control system 17 may further include a control device 42 such as a keypad, keyfob, card access, or similar device that controls a magnetic lock 50 that locks down the door 22 and prevents the door 22 from being opened when in the closed position. The control device 42 also actuates a local buzzer 43 for providing a local audio alarm near the door 22 in order to alert facility staff when certain conditions have occurred, such as the door 22 being opened in the presence of a patient wearing a patient monitoring device 20 who is detected by the motion detector 44. The control device 42 may also has a user interface (not shown), such as a numerical pad, that permits a user to enter an access code to unlock the magnetic lock 50 or reset the patient monitoring device 20 after actuation by the door access control system 17. In one embodiment, another control device 42 may be provided along the opposite or outside portion of the door 22 for controlling the operation of the door 22. In an embodiment, the control device 42 may be a 2000 Series e/eM Keypad manufactured by International Electronics Inc.

The door access control system 17 also includes a timer relay 46 that is actuated by a relay controller 26 whenever the second signal 97 transmitted by the patient monitoring device 20 is received by the relay controller 26 through either the inside antenna 40 or inside antenna 41. The timer relay 46 is coupled to the magnetic lock 50 through the control device 42 and permits the magnetic lock 50 to remain in a lock down mode that keeps the door 22 in the closed position and prevents the opening of door 22 until a predetermined amount of time has expired. For example, the timer relay 46 may be set for a 15 second time delay in which the door 22 will remain locked for that predetermined time period after the magnetic lock 50 has been actuated and the door 22 is in the closed position; however, the timer relay 46 may be set at other predetermined time periods, such as 30 seconds, 45 seconds, or other predetermined time periods. In one embodiment, the relay controller 26 may be a LE10 ROAM wireless receiver manufactured by BOSCH.

As further shown in FIG. 3, the monitoring system 16 may be coupled to a supervisory unit 25 that continuously monitors the operational status of the hardware and modules of the monitoring system 16. In one embodiment, the supervisory unit 25 is coupled to a fail-safe operation system 30 that is activated whenever the monitoring system 16 suffers either a hardware or module failure, such as when electrical power to the monitoring system 16 is interrupted or the modules that operate the monitoring system 16 become corrupted or disabled. The fail-safe operation system 30 is in communication with a paging transmitter system 38 that transmits signals containing data including the door location data 70, although in other embodiments other alarm notification data may be transmitted to one or more pagers 45 so that facility personnel are alerted whenever the monitoring system 16 has suffered a failure and the fail-safe operation system 30 has been activated.

Figure 7:
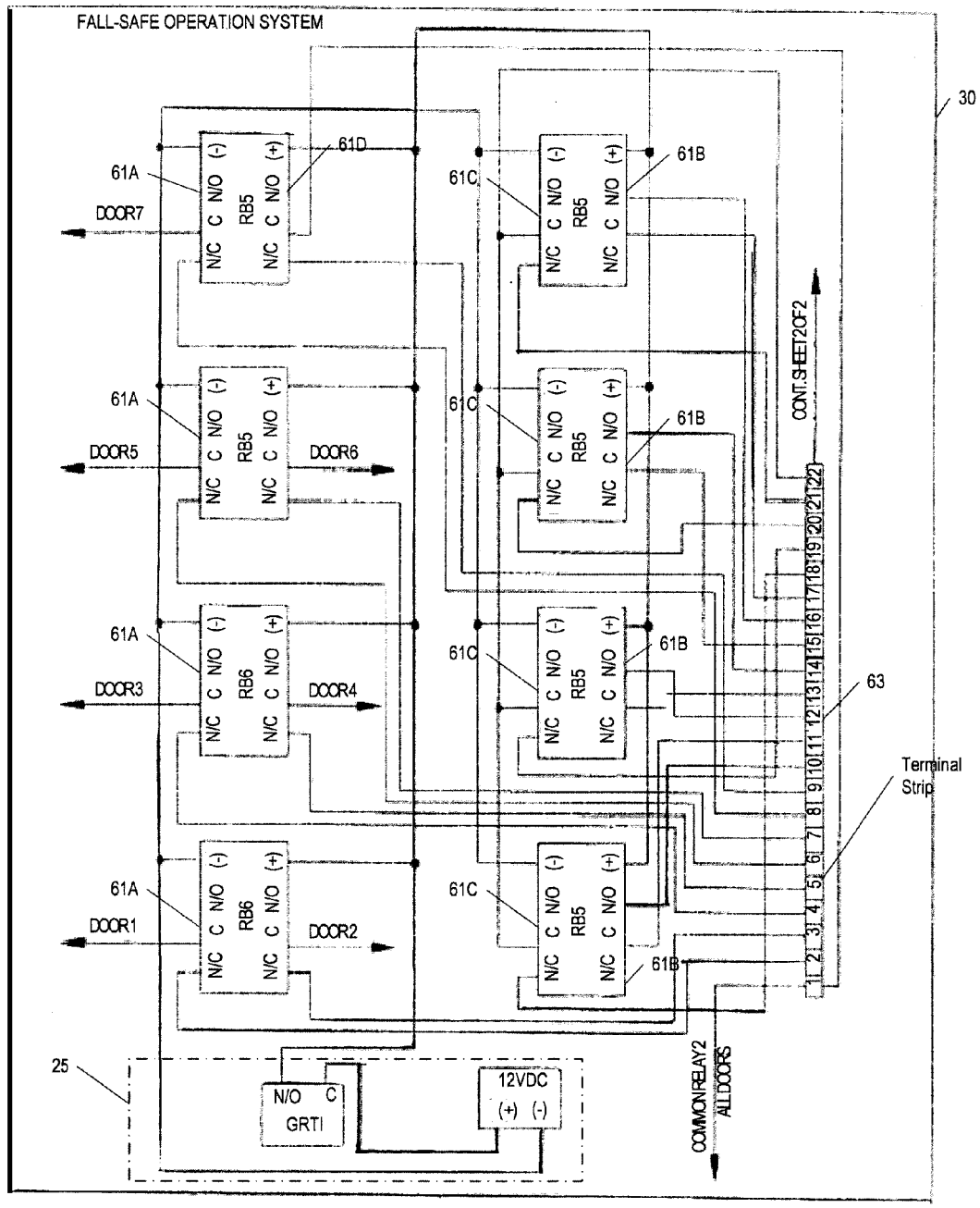
FIG. 7 is an electrical schematic diagram of the fail-safe operation system and supervisory unit for the patient monitoring system.

In one embodiment shown in FIG. 7, the fail-safe operation system 30 includes a plurality of relay components 61 that provide various fail-safe functions when the monitoring system 16 becomes inoperative. Specifically, the fail-safe operation system 30 includes relays 61A that are activated when the supervisory unit 25 detects the failure of the monitoring system 16. When the normally open relays 61A are closed by the supervisory unit 25 and a particular door 22 is subsequently opened, a respective relay 61A for that door 22 will be energized and a signal will be transmitted to the pagers 45 through the paging transmitter 38 identifying the door 22 that has been opened. The fail-safe operation system 30 further includes normally open relays 61B and 61C that are also operatively coupled to a respective door 22 and become closed when the supervisory unit 25 detects the failure of the monitoring system 16 and relay 61B then will energize and activate the inside antenna 40 of the door 22, while respective relay 61C will lock down the door 22 and prevent that door 22 from being opened. In one embodiment, the fail-safe operation system 30 when activated energizes the relay 61D that causes the paging transmitter 38 to transmit a message to pagers 45 that the monitoring system 16 has become inoperative. The fail-safe operation system 30 further includes a terminal strip 63 electronically coupled to a second relay 56 of the door access control unit 28. As noted above, the supervisory unit 25 is electrically coupled to the plurality of relays 61 of the fail-safe operation system 30 with the contacts of the supervisory unit 25 in a normally open position. The supervisory unit 25 also monitors the positive side of a 12-volt power supply in order to determine whether the monitoring system 16 is operational. In one embodiment, failure of the monitoring system 16 will cause the normally open contacts of the supervisory unit 25 to close, thereby closing the normally open relays 61 of the fail-safe operation system 30. In addition, when a door 22 is opened after activation of the fail-safe operation system 30, the paging transmitter system 38 will also transmit a signal to the pagers 45 with a notification that identifies the particular door 22 that has been opened. However, if a patient wearing a patient monitoring device 20 has passed through that opened door 22 the pagers 45 will only display the particular door 22 and cannot display the patient identification data 72 to the pagers 45 since the monitoring system 16 is not operable.

Figure 5:
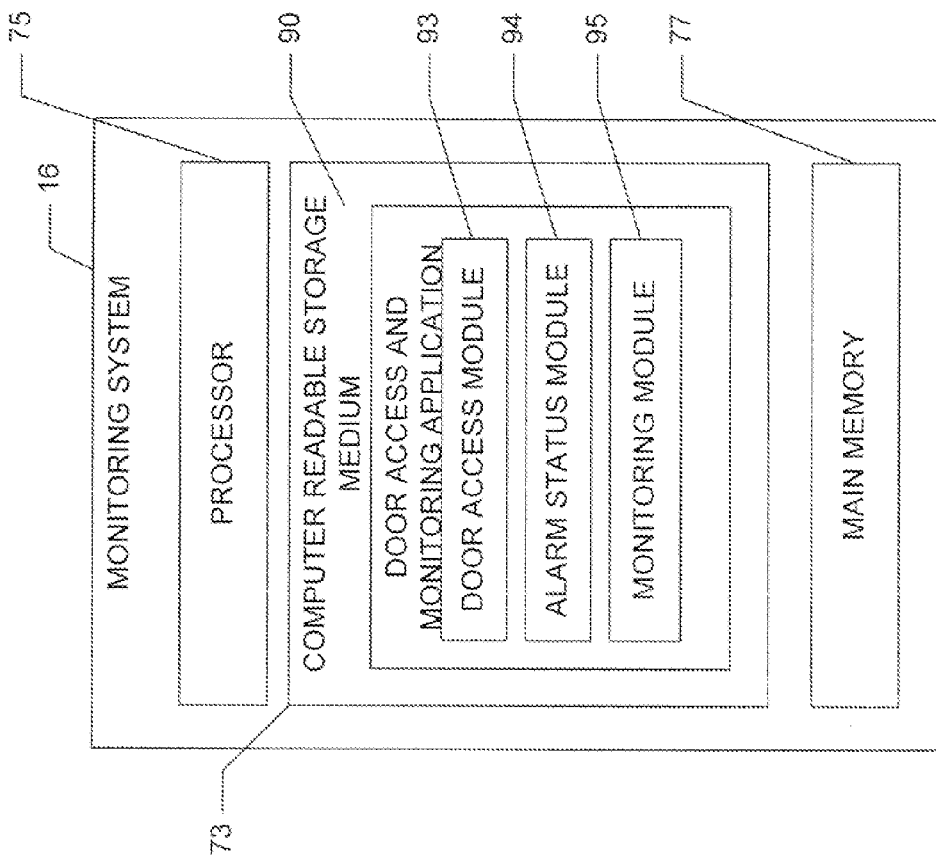
FIG. 5 is a simplified block diagram of a monitoring system for the patient monitoring system.

Referring to FIG. 5, one embodiment the monitoring system 16 may include a processor 75 capable of executing a door access and monitoring application 90 embodied in a computer-readable storage medium 73 stored in a main memory 77 of the monitoring system 16. The door access and monitoring application 90 may execute a plurality of modules, such as a door access module 93, alarm status module 94 and a monitoring module 95 when operating the monitoring system 16 as shall be discussed in greater detail below.

Figure 6:
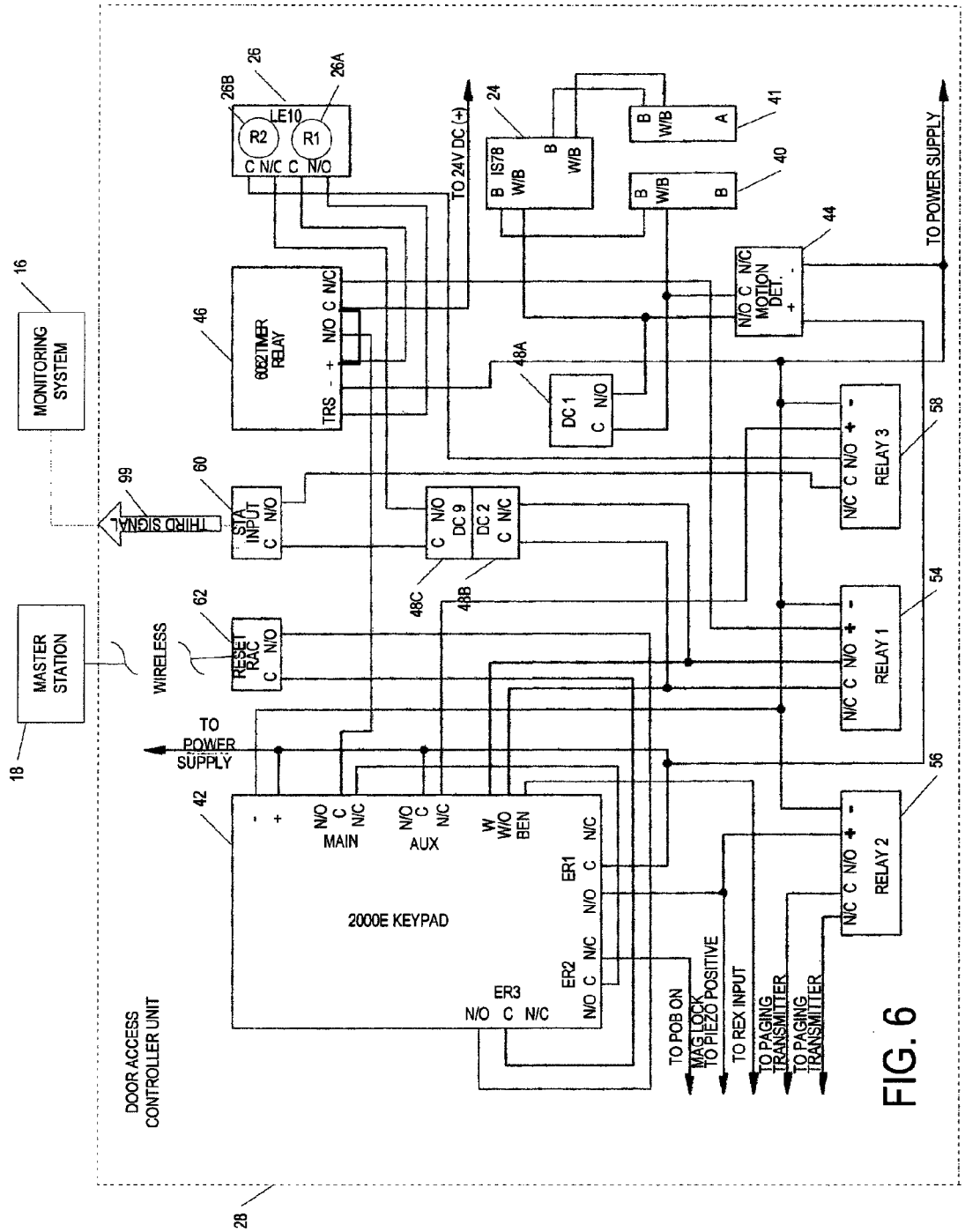
FIG. 6 is an electrical schematic diagram of a door access controller unit for the patient monitoring system.

In an example embodiment shown in FIG. 6, the door access control system 17 may include a door access controller unit 28 having an arrangement of various components for executing the modules 93, 94 and 95 of the door access and monitoring application 90. As shown, the control device 42 is electrically coupled to the timer relay 46, which is electrically coupled to the relay controller 26 having relays 26A and 26B. The relays 26A and 26B are triggered when the relay controller 26 is actuated after receiving the second signal 97 that is transmitted by the patient monitoring device 20 as described above. The relay 26A is electrically coupled with the timer relay 46 for actuating the magnetic lock 50 and locking down the door 22 for a predetermined time period.

The actuation of the timer relay 46 also energizes the first relay 54, which will then open its normally closed contacts. Because the first relay 54 is in a normally closed state and electrically coupled to the door input contacts on the control device 42, the open position of the door 22 will not activate an alarm or transmit a third signal 99 to the monitoring system 16 unless a person with a patient monitoring device 20 is also present and detected by the door access controller unit 28. As shown, the relay 26B of the relay controller 26 is electrically coupled to a STA INPUT device 60 through a third relay 58, which is energized whenever the relay 26B of the relay controller 26 is triggered.

The STA INPUT device 60 may be hardwired directly to the monitoring system 16 for communicating the third signal 99 to the master station 18 and the monitoring system 16 when the door contact 48C is triggered by the door 22 being placed in the open position as well as relay 58 being energized by the relay controller 26 upon receiving the second signal 97 transmitted by the patient monitoring device 20. In addition, door contact 48B is coupled to the door 22 such that opening the door 22 will trigger the door contact 48B and energize first relay 54. Door contact 48A may also be coupled to the door 22 which is triggered when the door 22 is opened, thereby actuating the inside antenna 40 and allowing the door transmitter 24 to transmit the first signal 96 to any nearby patient monitoring devices 20. This arrangement allows for the detection of any patient monitoring devices 20 in situations where either the motion detector 44 detects the presence of a person near the door 22, or the door 22 is opened from the outside, for example by a person entering the facility 15 in the presence of a person coupled to the patient monitoring device 20.

In one embodiment, the door access controller unit 28 may include a RESET RAC component 62, which is in wireless communication with the master station 18 and the monitoring system 16. In situations where the presence of the patient monitoring device 20 triggers the relay controller 26, the patient monitoring device 20 that triggered the door access control unit 30 must be subsequently reset. The patient monitoring device 20 is reset by entering the proper code into the respective control device 42 of door 22 which causes the monitoring system 16 to instruct the wireless transmitter (not shown) associated with the RESET RAC component 62 to transmit a signal that resets the patient monitoring device 20. This procedure ensures and documents that the patient coupled to the patient monitoring device 20 has been brought back into the facility 15 through the particular door 22 identified to the monitoring system 16.

In one embodiment, the second relay 56 of the access controller unit 28 is electrically coupled to first relay 54 and third relay 58. The second relay 56 may actuate the paging transmitter system 38 for transmitting signals to one or more pagers 45 when energized by the door access controller unit 28. The function of the door access controller unit 28 with respect to the first, second and third relays 54, 56 and 58 will be discussed in greater detail below.

The door access controller unit 28 is responsive to different scenarios in order to manage and control door access within the facility 15 as well as monitor any persons within close proximity of doors 22, especially patients coupled to a patient monitoring device 20. In a first scenario, a patient coupled to a patient monitoring device 20 is present (e.g., within close proximity of the door 22 to be detected by motion detector 44)

and the door 22 is in the open position. In a second scenario, a patient coupled to a patient monitoring device 20 is present and the door 22 is in the closed position. In a third scenario, a patient is not present but a person not coupled to the patient monitoring device 20 places the door 22 in the open position.

With respect to the first scenario when the patient is present and the door 22 is open, the inside antenna 40 is activated and the door transmitter 24 will transmit a first signal 96 to any nearby patient monitoring devices 20. If the relay controller 26 receives a second signal 97 from the patient monitoring device 20 and the door 22 is open, the STA INPUT device 60 transmits a third signal 99 encoded with door location data 70 and patient identification data 72 directly to the monitoring system 16. However, if the person detected by the door access control system 17 is not coupled to a patient monitoring device 20, such as a visitor or facility employee, a second signal 97 is not transmitted to the relay controller 26 since a patient with a patient monitoring device 20 is not present, thereby preventing any false alarms from occurring.

With respect to the second scenario when the patient coupled to a patient monitoring device 20 is detected and the door 22 is closed, the STA INPUT device 60 has not been triggered since the door 22 is in the closed position, despite the fact that the motion detector 44 has detected the presence of a person coupled to a patient monitoring device 20. As noted above, the transmission of the second signal 97 encoded with door location data 70 and user identification data 72 by the patient monitoring device 20 to the monitoring system 16 is made in response to the first signal 96 being transmitted by the door transmitter 24, which is received by the patient monitoring device 20.

However, since the door contacts 48 have not been triggered, the STA INPUT device 60 cannot transmit a third signal 99 to the monitoring system 16. Upon receipt of the second signal 97 transmitted by the patient monitoring device 20, the monitoring system 16 will attempt to match the data encoded in the second signal 97 with any third signals 99 transmitted to the monitoring system 16 by the door access control unit 28; however, since no match can be made since no third signal 99 was ever transmitted the alarm status module 94 will clear the second signal 97 using the alarm status module 94 so that neither the master station 18 nor the slave stations 19 will display any of the data encoded in the second signal 97. As such, the monitoring system prevents false alarms from being generated by the presence of a person with a patient monitoring device 20 being in proximity to any door 22 in the facility 15 that is in a closed or locked down position. In one embodiment, the presence of a patient coupled to a patient monitoring device 20 can cause the door access control system 17 to automatically lock down the door 22 when a person is detected within proximity of the door 22 by the motion detector 44, thereby preventing passage of the person through door 22 unless that person can enter an access code into the control device 42. In other embodiments, the door 22 may be normally locked down at all times by the door access module 90 and monitoring module 95, unless the appropriate code is entered into the control device 42 for causing the magnetic lock 50 to actuate and permit the door 22 to be opened. In this scenario when the door 22 is normally locked, the alarm status module 94 will not display the data 70 and 72 encoded in the second signal 99 transmitted by the patient monitoring device 20 to the monitoring system 16.

With respect to the third scenario when the patient is not present, but a person not coupled to the patient monitoring device 20 opens the door 22, the door contacts 48 will be triggered, but the STA INPUT device 60 will not transmit the third signal 99 to the monitoring system 16 since the relay controller 26 has not received the second signal 97 from any patient monitoring device 20 within vicinity of the inside antenna 40. As such, only a first signal 96 generated by the presence of the person triggering the motion detector 44 will be transmitted, but no third signal 99 will be transmitted since no second signal 97 was ever transmitted since no person coupled to a patient monitoring device 20 was detected by the door access control system 17.

Figure 8:
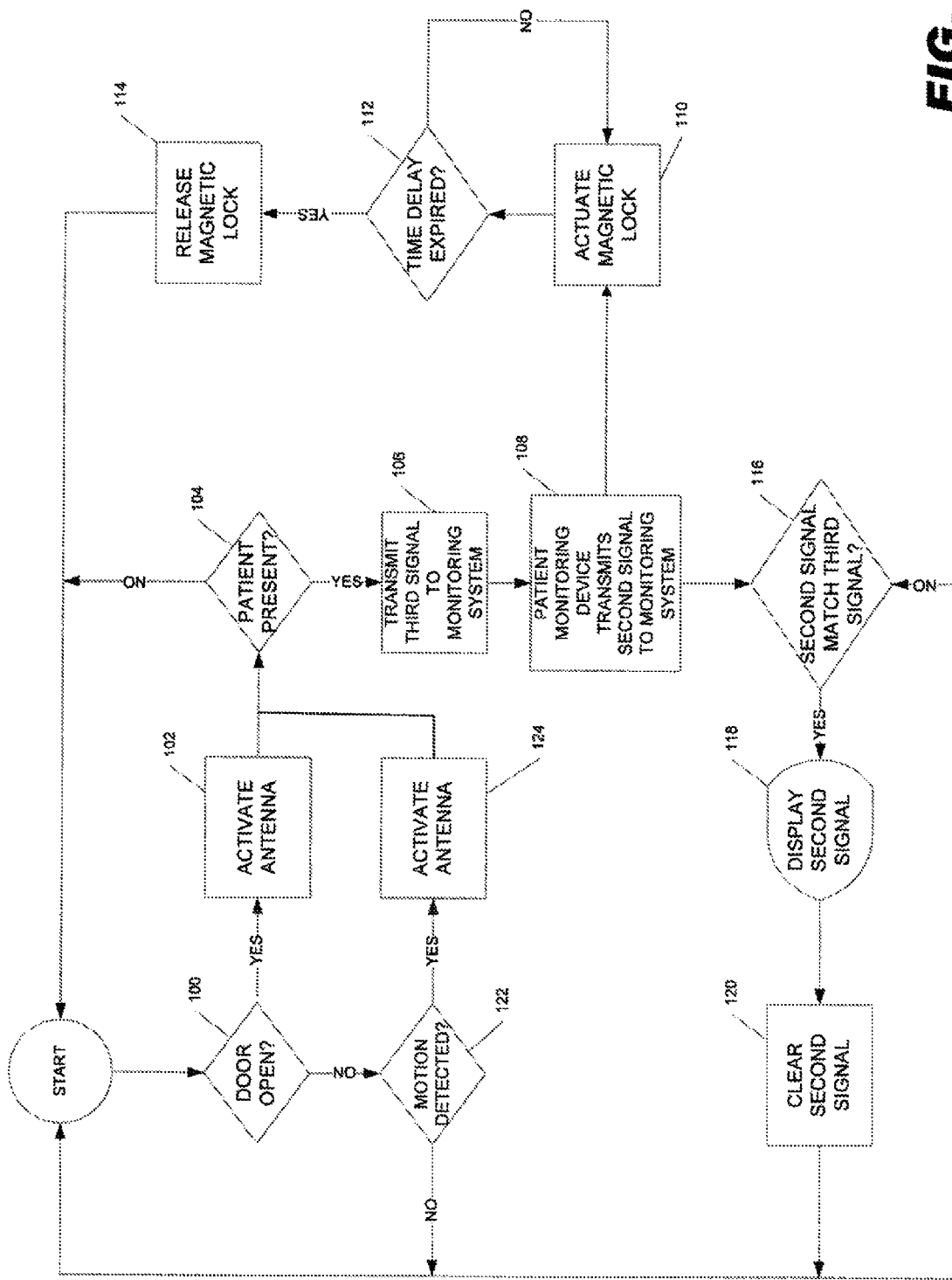
FIG. 8 is a flow chart illustrating the methods for patient monitoring and door access for the patient monitoring system.

Referring to FIGS. 5 and 8, the operation of the door access control application 90 that is stored in the computer-readable storage medium 73 and executed by processor 75 will be discussed in greater detail. As noted above, the door access control application 90 includes the door access module 93 that controls the operation of the door access control system 17, the alarm status module 94 that either displays or clears the second signal 97, and the monitoring module 95 that provides patient monitoring and door access functions.

In one embodiment, the door access and monitoring application 90 determines at decision point 100 whether the door 22 is open or not. If the door 22 is open, then at block 102 the door access control unit 28 activates the inside antenna 40. Once the inside antenna 40 is activated, the application 90 determines at decision point 104 whether a patient is present and in close proximity to the door 22. As discussed above, the door access control system 17 determines whether a patient with a patient monitoring device 20 is present by receiving the second signal 97 in response to the first signal 96 originally transmitted by the door transmitter 24. If a patient coupled to a patient monitoring device 20 is not present, then the door access and monitoring application 90 returns to START; however, if a patient coupled to a patient monitoring device 20 is present, then at block 106, the door access control unit 28 transmits the third signal 99 to the monitoring system 16. At block 108, the patient monitoring device 20 will transmit the second signal 97 to the patient monitoring system 16 via the wireless network 13. Once the patient monitoring device 20 has transmitted the second signal 97, then at block 110 the door access and monitoring application 90 will actuate the magnetic lock 50 will lock down the door 22. Once the magnetic lock 50 has been activated, then at decision point 112 the timer relay 46 determines whether the predetermined time delay has expired. If the time delay has expired, then at block 114, the timer relay 46 deactivates the magnetic lock 50 and permits the door 22 to be opened before returning to START. In addition, when the patient monitoring device 20 has transmitted the second signal 97 to the monitoring system 16, then the door access and monitoring application 90 determines at decision point 116 whether the data encoded in the second signal 97 matches the data encoded in the third signal 99. If there is a match between signals 97 and 99, then at block 118, the door access and monitoring application 90 displays the door location data 70 and patient identification data 72 at master station 18 and slave units 19. However, if there is no match between the two signals 97 and 99, the alarm status module 94 will clear the signals and no display of data will occur at the master station 18 and slave stations 19.

However, if the door access and monitoring application 90 determines at decision point 102 that the door is closed, then at decision point 122, application 90 will determine whether a person is present and in close proximity to the door 22. If not, then the door access and monitoring application 90 returns to START; however, if a person is present, then the inside antenna 40 is activated at block 124 before proceeding to block 108 as discussed above.

Figure 9:
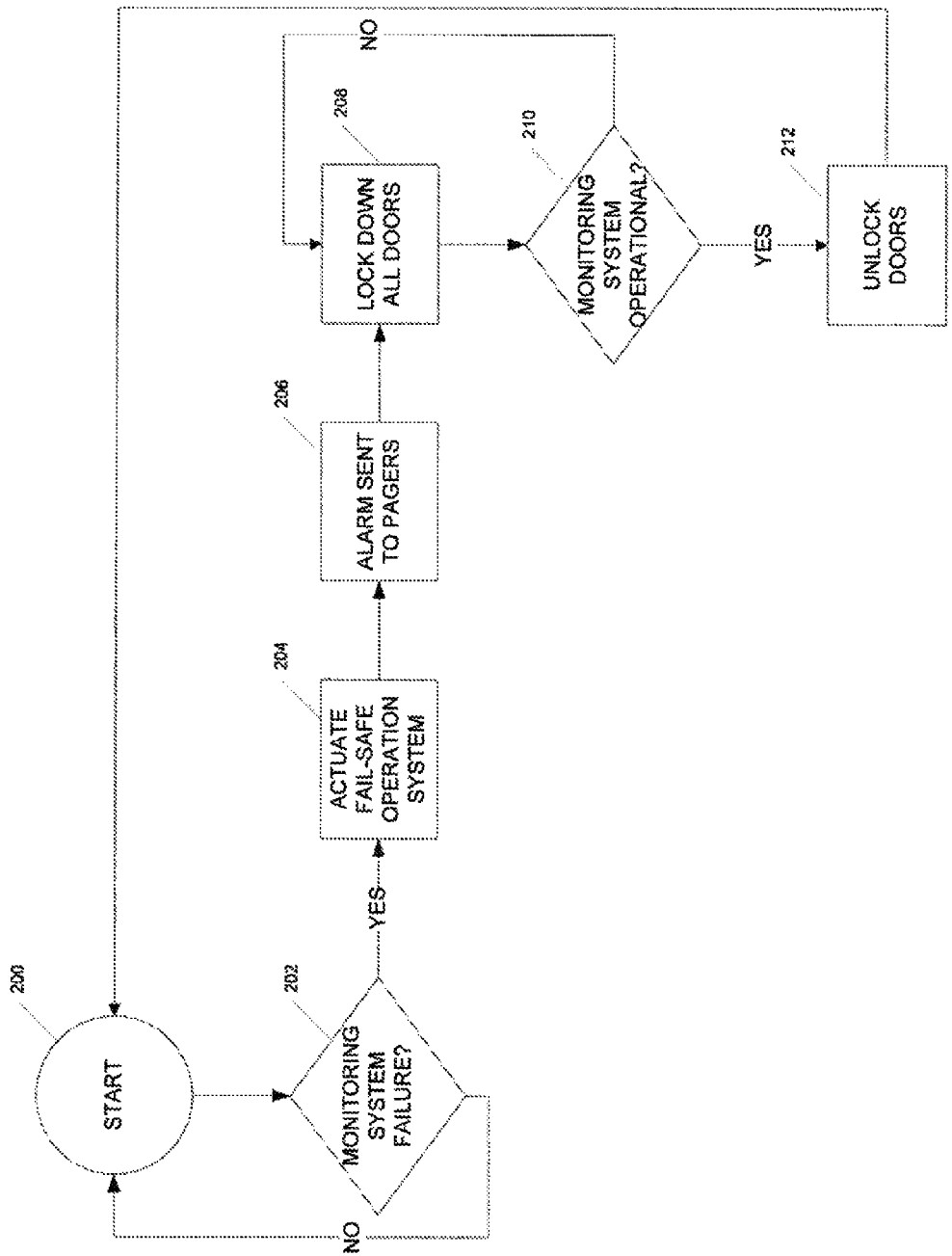
FIG. 9 is a flow chart illustrating the methods for fail safe operation of the patient monitoring system.

Referring to FIG. 9, the operation of the fail-safe operation system 30 and the supervisory unit 25 will be discussed in greater detail. In one embodiment, the supervisory unit 25 continuously monitors the operational state of the monitoring system 16 initiated at block 200. At decision point 202, the supervisory unit 25 determines whether the monitoring system 16 has failed. If the monitoring system 202 has not failed, the fail-safe operation system 30 returns to block 200; however, if the supervisory unit 28 detects the failure of the monitoring system 202, the supervisory unit 25 will actuate the fail-safe operation system 30 by energizing relays 61. At block 206, the fail-safe operation system 30 causes the second relay 56 of the door access controller unit 28 to be energized that transmits an alarm signal to the pagers 45 through the paging transmitter 38, while at block 208 the fail-safe operation system 30 will lock down all of the doors 22 within the facility 15. Once the doors 22 are locked down, then at decision point 210 the application 90 determines if the monitoring system 16 is operational. If the monitoring system 16 is still inoperative, then the fail-safe operation system 30 returns to block 208 to continue the lock down of doors 22 until the monitoring system 16 becomes operational; however, if the monitoring system 16 has become operational then at block 212, the timer relay 46 unlocks the doors 22 and then returns to block 200.

Figure 10:
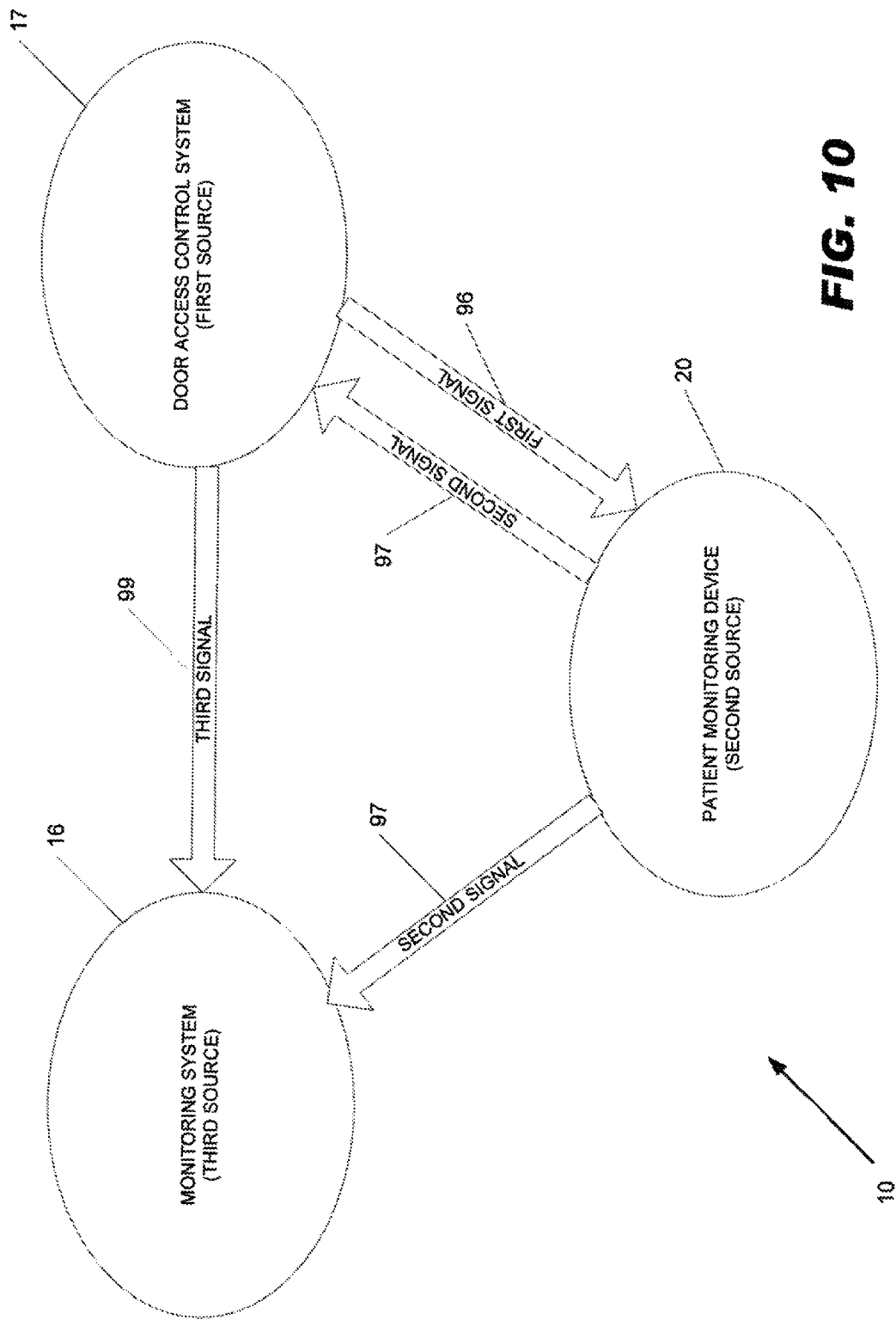
FIG. 10 is a simplified block diagram illustrating the various signals generated between different sources of the patient monitoring system.

Referring to FIG. 10, in one embodiment of the patient monitoring system 10 the door access control system 17 may be considered a first source for transmitting the first signal 96 coupled to a patient encoded with door location data 70 when the presence of a person is detected by the motion detector 44, while the patient monitoring device 20 may be considered a second source that receives the first signal 96 transmitted by the first source. In response to receiving the first signal 96, the second source simultaneously transmits the second signal 97 encoded with the door location data 70 and patient identification data 72 to a third source, such as the monitoring system 16, as well as the first source, such as the door access control system 17. When the first source (door access control system 17) receives the second signal 97 and detects that the door 22 is in the open position, the first source generates the third signal 99 The third source (monitoring system 16) then compares the door location data 70 encoded in the second signal 97 with the door location data 70 encoded in the third signal 99, and if the door location data 70 of the second signal 97 matches the door location data 70 of the third signal 99, the master station 18 and the slave units 19 will display the door location data 70 and the patient identification data 72 of the third signal. In other embodiments, alarm notification data, such as the patient's name, age, gender, and/or the time the door 22 was accessed may be displayed.

Figure 11:
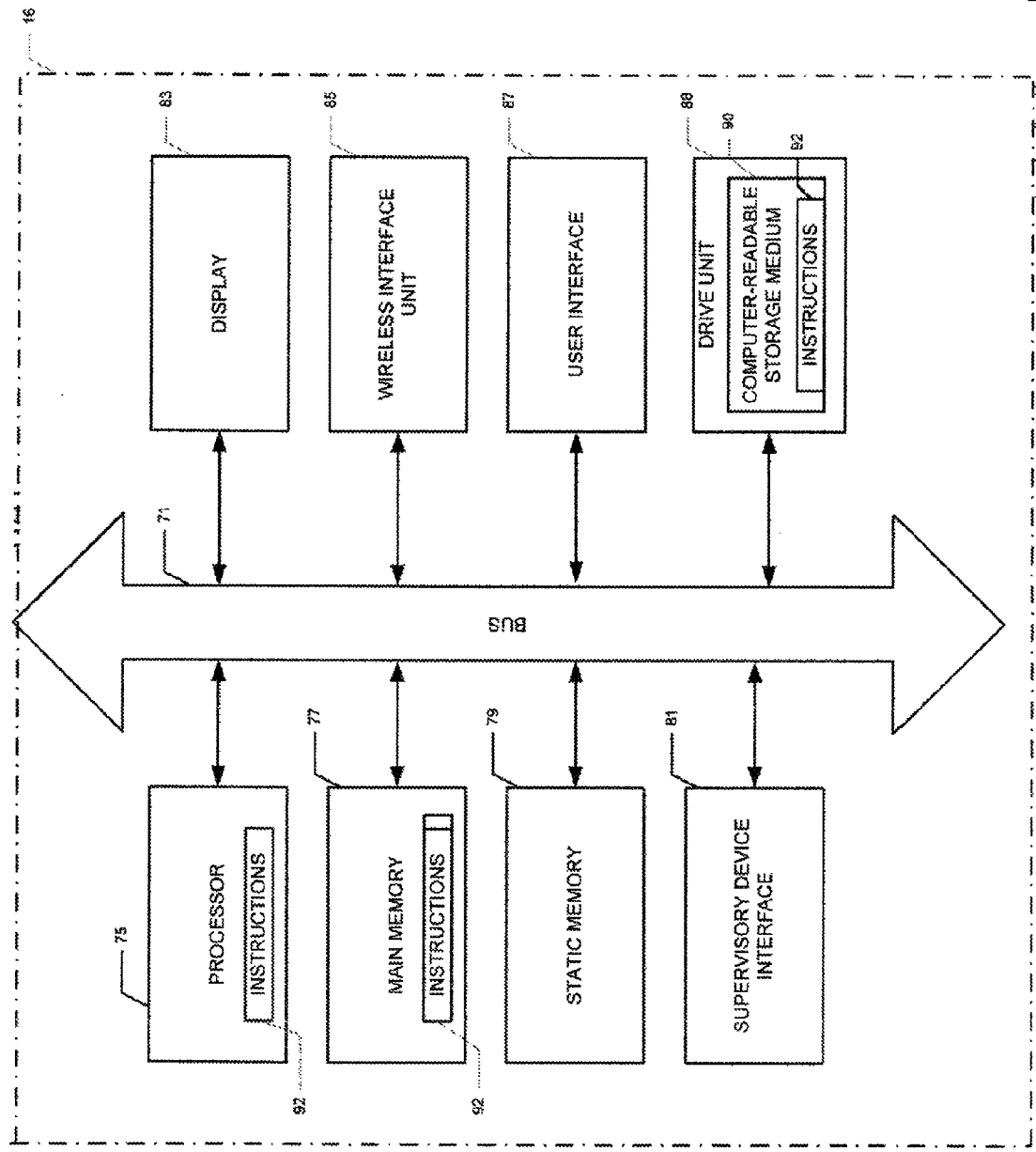
FIG. 11 is a simplified block diagram of a machine in an example form of a computer system within which a set of instructions for causing the machine to perform any one or more of the methodologies discussed herein.

FIG. 11 shows a simplified block diagram of a machine in the example form of a computer system 200 within which a set of instructions may be executed causing the machine to perform any one or more of the methods, processes, operations, or methodologies discussed herein. The monitoring system 16 may include the functionality of one or more computer systems 200.

In an example embodiment, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 200 includes a processor 75 (e.g., a central processing unit (CPU), a graphics processing unit (GPU), or both), a main memory 77 and a static memory 79, which communicate with each other via a bus 71. The computer system 200 may further include a display 83 (e.g., a liquid crystal display (LCD) or a cathode ray tube (CRT)). The computer system 200 also includes a user interface 87 (e.g., keyboard and mouse), a drive unit 88, a wireless interface unit 85, and a supervisory device interface 81 for interfacing with the supervisory unit 25.

The drive unit 88 includes a computer-readable storage medium 90 on which is stored one or more sets of instructions 92 embodying any one or more of the methodologies or functions described herein. The instructions 92 (e.g., software) may also reside, completely or at least partially, within the main memory 77 during execution thereof by the computer system 200, the main memory 77 and the processor 75 also constituting computer-readable storage medium or machine-readable media.

While the machine-readable storage medium 1022 is shown in an example embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical media, and magnetic media.

Certain systems, apparatus, applications or processes are described herein as including a number of modules. A module may be a unit of distinct functionality that may be presented in software, hardware, or combinations thereof. When the functionality of a module is performed in any part through software, the module includes a machine-readable medium. The modules may be regarded as being communicatively coupled.

The inventive subject matter may be represented in a variety of different embodiments of which there are many possible permutations.

Thus, methods and systems for door access and patient monitoring have been described herein. Although embodiments of the patient monitoring system have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods can be performed continuously.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
    transmitting a first signal from a first source indicating when a person is detected within a predetermined distance from a door, the first signal being encoded with door location data that identifies the door;
    receiving the first signal at a second source, the second source being coupled to the person;
    transmitting a second signal from the second source to the first source and a third source, the second signal being encoded with the door location data and identification data of the person coupled to the second source;
    receiving the second signal at the first source and the third source and transmitting from the first source a third signal to the third source if the door is in an open position, wherein the third signal is encoded with the door location data of the door and identification data of the person coupled to the second source;
    determining whether the door location data encoded in third signal matches the door location data encoded in the first signal; and
    displaying the door location data and the identification data of the second signal if the door location data encoded in the third signal matches the door location data encoded in the second signal.

2. The method of claim 1, further comprising:
    transmitting the second signal to the third source by the second source in response to receiving the first signal from the first source.

3. The method of claim 1, further comprising:
    locking down the door when the second source coupled to the person comes within a predetermined distance of the door.

4. The method of claim 3, wherein the door is locked down for a predetermined time period.

5. The method of claim 1, further comprising:
    preventing the display of the door location data and identification data encoded in the second signal if the door location data encoded in the third signal does not match the door location data encoded in the second signal.

6. The method of claim 1, further comprising:
    transmitting the third signal for display on one or more pagers if the door location data encoded in the third signal matches the door location data encoded in the second signal.

7. The method of claim 6, wherein the one or more pagers display the door location data and the identification data encoded in the second signal.

8. The method of claim 1, wherein the first source is a door access control system that controls and monitors access to the door and the second source is a monitoring device coupled to the person, wherein the monitoring device includes the identification data of the person coupled to the monitoring device.

9. The method of claim 1, further comprising:
    clearing the second signal from the display after the door location data and the identification data are displayed.

10. The method of claim 1, further comprising:
    resetting the second source at the first source after the door location data and identification data are displayed, wherein resetting the second source permits the second source to transmit another second signal in response to receiving another first signal from the first source.

11. The method of claim 1, further comprising:
    activating an antenna prior to transmitting the first signal from the first source, wherein the antenna is activated if the person is detected within the predetermined distance from the door and wherein the antenna permits the first source to transmit the first signal and receive the second signal.

12. The method of claim 1, wherein the first source is a door access control system that controls and monitors access to the door and the second source is a monitoring device coupled to the person, wherein the monitoring device includes the identification data of the person coupled to the monitoring device.

13. The method of claim 1, further comprising:
    clearing the second signal from the display after the door location data and the identification data are displayed.

14. A method comprising:
    determining whether a door is in the open or closed position;
    transmitting a first signal from a first source if the door is in the open position, the first signal being encoded with door location data identifying the door that is in the open position;
    receiving the first signal at a second source if a person is within a predetermined distance of the door and the person is coupled to the second source;
    encoding a second signal with an identification data identifying the person coupled to the second source and the door location data encoded in the first signal;
    transmitting the second signal to the first source and a third source in response to receiving the second signal by the second source from the first source;
    encoding a third signal with the identification data encoded in the second signal and the door location data of the door in the open position;
    transmitting the third signal to the third source;
    determining at the third source whether the door location data encoded in the second signal matches the door location data encoded in the third signal; and
    displaying the door location data and the identification data if the door location data encoded in the first signal matches the door location data encoded in the third signal.

15. The method of claim 14, further comprising:
    transmitting the second signal to the third source by the second source in response to receiving the first signal from the first source.

16. The method of claim 14, further comprising:
    locking down the door when the second source coupled to the person comes within a predetermined distance of the door.

17. The method of claim 16, wherein the door is locked down for a predetermined time period.

18. The method of claim 16, further comprising:
    preventing the display of the door location data and identification data encoded in the second signal if the door location data encoded in the third signal does not match the door location data encoded in the second signal.

19. The method of claim 14, further comprising:
transmitting the third signal for display on one or more pagers if the door location data encoded in the third signal matches the door location data encoded in the second signal.

20. The method of claim 19, wherein the one or more pagers display the door location data and the identification data encoded in the second signal.

21. A system for door access and patient monitoring comprising:
door access control system coupled to a door operable between an open position and a closed position, the door access control system including a means for detecting a person within a predetermined distance from the door, the door access control system further including an antenna for transmitting a first signal encoded with door location data when the person comes within a predetermined distance from the door, wherein the door location data identifies the location of the door;
monitoring device coupled to the person, the monitoring device including a receiver for receiving the first signal transmitted by the door access control system and a transmitter for transmitting a second signal encoded with the door location data and identification data that identifies the person coupled to the monitoring device, wherein the antenna of the door access control system receives the second signal transmitted by the monitoring device, and wherein the door access control system transmits a third signal encoded with the door location data and the identification data upon receiving the second signal from the monitoring device; and
monitoring system for receiving the second signal transmitted by the monitoring device and the third signal transmitted by the door access control system, the monitoring system including a processor for executing an application stored on a computer-readable storage medium that compares the door location data encoded in the second signal with the door location data encoded in the third signal for determining whether to display the door location data and the identification data encoded in the second signal.

22. The system of claim 21, further comprising:
a wireless network in communication with the monitoring device for communicating the second signal to the monitoring system, the wireless network including a master station in communication with one or more slave units.

23. The system of claim 21, wherein the antenna is actuated upon detection of a person within the predetermined distance from the door.

24. The system of claim 21, wherein the antenna is actuated upon the door being in the open position.

25. The system of claim 21, wherein the monitoring system locks down the door upon detection of the person within the predetermined distance of the door.

26. The system of claim 21, wherein the door access control system further comprises:
door access control unit having a door transmitter electronically coupled to the antenna for generating the first signal for transmission by the antenna and a relay controller for receiving the second signal from the antenna, wherein upon receiving the second signal the relay controller locks down the door.

27. The system of claim 26, wherein the door access control unit further comprises:
STA INPUT device electronically coupled to the relay controller, the STA INPUT device generating the third signal and transmitting the third signal to the monitoring system only when the door is in the open position and the relay controller receives the second signal from the monitoring device.

28. The system of claim 26, wherein the monitoring system is electronically coupled to a supervisory unit for monitoring the operational state of the monitoring system, the supervisory unit being electronically coupled to a fail-safe operation system that is actuated only when the supervisory unit detects the operational failure of the monitoring system.

29. The system of claim 28, wherein the fail-safe operation system includes a first plurality of relays, a second plurality of relays and a third plurality of relays, each of the first plurality of relays being electronically coupled to a respective door for locking down the respective door only when the supervisory unit actuates the fail-safe operation system, each of the second plurality of relays being electronically coupled to a paging transmitter for transmitting activating the antenna for each respective door, and the third plurality of relays being electronically coupled to a respective antenna for each respective door for actuating the antenna.

* * * * *